US010317269B2

(12) United States Patent
Shiroyama et al.

(10) Patent No.: US 10,317,269 B2
(45) Date of Patent: Jun. 11, 2019

(54) FLOW RATE VERIFICATION UNIT

(71) Applicant: CKD CORPORATION, Komaki-shi, Aichi (JP)

(72) Inventors: Naoya Shiroyama, Kasugai (JP);
Akihito Sugino, Gunpo-Si (KR);
Minoru Ito, Kasugai (JP)

(73) Assignee: CKD CORPORATION, Komaki-shi (JP)

( * ) Notice: Subject to any disclaimer, the term of this patent is extended or adjusted under 35 U.S.C. 154(b) by 159 days.

(21) Appl. No.: 15/516,164

(22) PCT Filed: Nov. 5, 2015

(86) PCT No.: PCT/JP2015/081168
§ 371 (c)(1),
(2) Date: Mar. 31, 2017

(87) PCT Pub. No.: WO2016/072451
PCT Pub. Date: May 12, 2016

(65) Prior Publication Data
US 2017/0299420 A1 Oct. 19, 2017

(30) Foreign Application Priority Data
Nov. 5, 2014 (JP) ................................. 2014-225018

(51) Int. Cl.
*G01F 25/00* (2006.01)
*G01N 7/14* (2006.01)
(52) U.S. Cl.
CPC ...... *G01F 25/0007* (2013.01); *G01F 25/0053* (2013.01); *G01F 25/0084* (2013.01); *G01N 7/14* (2013.01)

(58) Field of Classification Search
CPC .......... G01N 1/38; G01N 15/06; G01N 19/10; G01N 21/25; G01N 33/24; G01F 1/00; G01F 5/00; G01F 25/0007
See application file for complete search history.

(56) References Cited

U.S. PATENT DOCUMENTS 7,966,875 B2 * 6/2011 Proett .................... E21B 49/10
73/152.22
2009/0019943 A1 1/2009 Ozawa et al.
2014/0013838 A1 1/2014 Sawada et al.

FOREIGN PATENT DOCUMENTS

CN 101395453 A 3/2009
CN 103282748 A 9/2013
(Continued)

OTHER PUBLICATIONS

Dec. 8, 2015 International Search Report issued in Patent Application No. PCT/JP2015/081168.
(Continued)

Primary Examiner — David Z Huang
(74) Attorney, Agent, or Firm — Oliff PLC

(57) ABSTRACT

A flow rate verification unit that uses the pressure variation value per unit time of a pressure measurement value measured by a pressure gauge and a temperature measurement value measured by a thermometer in a state where a second shut-off valve is closed to calculate the volume between a flow-rate control valve and the second shut-off valve and verifies the flow rates of mass flow controllers one at a time, wherein a first verification side connection part attachably and detachably connected to an integrated gas unit is provided upstream from the pressure gauge and a serially connected verification gas input valve, verification side mass flow controller, and verification side flow rate control valve are provided in parallel with the second shut-off valve.

4 Claims, 8 Drawing Sheets

(56) References Cited

FOREIGN PATENT DOCUMENTS

| | | |
|---|---|---|
| JP | 2006-337346 A | 12/2006 |
| JP | 2011-064707 A | 3/2011 |
| JP | 2012-141254 A | 7/2012 |

OTHER PUBLICATIONS

Feb. 27, 2019 Office Action issued in Chinese Patent Application No. 201580058651.9.

* cited by examiner

FLOW RATE VERIFICATION UNIT

CROSS-REFERENCE TO RELATED APPLICATIONS

This is a US national phase application based on the PCT International Patent Application No. PCT/JP2015/081168 filed on Nov. 5, 2015, and claiming the priority of Japanese Patent Application No. 2014-225018, filed on Nov. 5, 2014, the entire contents of which are herewith incorporated by reference.

TECHNICAL FIELD

The present invention relates to a flow rate verification unit to verify a flow rate of each of a plurality of mass flow controllers provided in an integrated gas unit.

BACKGROUND ART

An integrated gas unit is formed by integrating a plurality of gas supply lines. The integrated gas unit is, for example, connected to a reaction vessel to regulate one or more than one gas which is to be supplied to the vacuumed reaction vessel through the gas supply lines. A flow rate of operation gas to be supplied to the reaction vessel exerts influence on product quality. For this reason, each of the gas supply lines includes a mass flow controller to measure the flow rate and a flow rate regulation valve operative to make a flow rate value measured by the mass flow controller agree with a set flow rate. The mass flow controller is, for example, configured to measure the flow rate based on a temperature difference between an upstream side and a downstream side of a thin inner pipe through which the operation gas flows. When products of the operation gas adhere to an inside wall of the inner pipe and thereby an inner diameter of the pipe changes, there occurs an error (difference) in the measured value measured by the mass flow controller. In response to this, the integrated gas unit is configured to verify each flow rate of the respective mass flow controllers one at a time by use of a flow rate verification unit.

FIG. 8 is a circuit diagram of a conventional flow rate verification unit 101 and a conventional integrated gas unit 110. The integrated gas unit 110 is provided with a purge gas line 111 to regulate purge gas and first to third gas supply lines 121A, 121B, and 121C. The purge gas line 111 is provided with a purge gas input port 117 to input the purge gas and connected with a regulator 112, a Bourdon pressure gauge 113, a pressure gauge 114, a first purge valve 115, and a second purge valve 116 in series in this order from an upstream side. The first gas supply line 121A is provided with a gas input port 127A to input first gas and connected with a pressure gauge 122A, a gas input valve 123A, a mass flow controller (MFC) 124A, and a flow rate regulation valve 125A in series in this order from the upstream side. The first gas supply line 121A is further provided with a purge gas input valve 126A between the gas input valve 123A and the mass flow controller 124A to control input of the purge gas which has branched off and flown from the purge gas line 111. The second and third gas supply lines 121B and 121C are configured similarly to the first gas supply line 121A. The purge gas line 111 and the first to third gas supply lines 121A to 121C are arranged in parallel to a common output valve 131 via a common passage 130.

The flow rate verification unit 101 is provided with a first shutoff valve 102, a pressure gauge 103, a thermometer 104, and a second shutoff valve 105. The first shutoff valve 102 is connected to the common passage 130. When flow rate verification of the mass flow controller 124A is to be performed, for example, the flow rate verification unit 101 is controlled to bring each of the gas input valves 123A to 123C, the second purge valve 116, the flow rate regulation valves 125B and 125C, the common output valve 131, and the second shutoff valve 105 into the valve-closed state and bring each of the first purge valve 115, the purge gas input valve 126A, the flow rate regulation valve 125A, and the first shutoff valve 102 into the valve-open state. The flow rate verification unit 101 subsequently executes the control to flow purge gas into the mass flow controller 124A so that the second purge valve 116, the flow rate regulation valves 125A to 125C, the common output valve 131, and the second shutoff valve 105 are filled with the purge gas. The flow rate verification unit 101 obtains a pressure increased value during a measurement time from a pressure measured value measured by the pressure gauge 103 and calculates an absolute flow rate of the mass flow controller 124A from values of the obtained pressure increased value, the temperature measured value measured by the thermometer 104, the measurement time, and a volume V among the second purge valve 116, the flow rate regulation valves 125A to 125C, the common output valve 131, and the second shutoff valve 105. The flow rate verification unit 101 further obtains the difference between the calculated absolute flow rate and the set flow rate and calibrates the set flow rate in a case that the difference is within an allowable range between a normal range and an abnormal range. When the difference falls in the abnormal range, the flow rate verification unit 101 makes an indication to indicate an instruction to replace the mass flow controller 124A.

Each integrated gas unit 110 has the same circuit configuration, but a volume V1 among the second purge valve 116, the flow rate regulation valves 125A to 125C, the common output valve 131, and the first shutoff valve 102 varies according to units by tolerances of constituent components, assembling tolerances, and other reasons (the volume V1 is also called "tank volume V"). Variations in the tank volume V1 correspond to variations in the volume V, leading to a decline in accuracy of the flow rate verification.

To address the above, the conventional flow rate verification unit 101 is configured to, for example, bring the first purge valve 115, the purge gas input valve 126A, the flow rate regulation valve 125A, and the first shutoff valve 102 into the valve-open state, bring the flow rate regulation valves 125B and 125C, the purge gas input valves 126B and 126C, the common output valve 131, and the second shutoff valve 105 into the valve-closed state, and then supply purge gas to the purge gas line 1 and obtain the pressure increased value per unit time from when the pressure gauge 103 measures the predetermined initial pressure to when the pressure gauge 103 measures the target value. The volume V is thus calculated based on the pressure increased value and the temperature measurement value measured by the thermometer 104. A volume V2 between the first shutoff valve 102 and the second shutoff valve 105 has been known in advance (the volume V2 is also called "known volume V2"), and hence the flow rate verification unit 101 calculates the tank volume V1 by subtracting the known volume V2 from the volume V. As a result of this, the variations in the tank volume V1 are reflected on the flow rate verification of the mass flow controllers 124A to 124C (see Patent Document 1, for example).

RELATED ART DOCUMENTS

Patent Documents

Patent Document 1: JP 2011-64707 A

SUMMARY OF INVENTION

Problems to be Solved by the Invention

The conventional flow rate verification unit 101 is configured to measure the volume V (the tank volume V1) by use of the mass flow controller 124A of the integrated gas unit 110, for example. When the mass flow controllers 124A to 124C are used for gas regulation, there is a possibility that products may adhere to an inner pipe. The conventional flow rate verification unit 101 therefore needs to calculate the volume V (the tank volume V1) before shipping or start of using the integrated gas unit 110. The volume V (the tank volume V1) is specific to the corresponding integrated gas unit 110, and accordingly, the conventional flow rate verification unit 101 has been provided one for each of the integrated gas units 110 in order to assure accuracy of the flow rate verification. The flow rate verification is performed at regular intervals, but, for example, only once a week, and hence the flow rate verification units have not been utilized effectively.

The present invention has been made to solve the above problem and has a purpose of providing a flow rate verification unit which is detachably attached to any one of a plurality of integrated gas units to perform flow rate verification for each of a plurality of the integrated gas units.

Means of Solving the Problems

One aspect of the present invention has the following configuration.

(1) A flow rate verification unit to perform flow rate verification for an integrated gas unit provided with a plurality of gas supply lines arranged in parallel, each of the gas supply lines including a mass flow controller and a flow rate regulation valve, the flow rate verification unit comprising a pressure gauge, a thermometer, and a shutoff valve which are arranged in series, and the flow rate verification unit being configured to verify a flow rate of each mass flow controller one at a time by calculating a volume between the flow rate regulation valve and the shutoff valve by use of a pressure variation value of a pressure measured value per unit time measured by the pressure gauge and a temperature measured value measured by the thermometer in a state in which the shutoff valve is closed, wherein the flow rate verification unit further includes a connection part provided on an upstream side of the pressure gauge, the connection part being configured to be detachably connected with the integrated gas unit, a verification gas input valve for controlling input of verification gas, a verification-side mass flow controller for measuring a flow rate of the verification gas, and a verification-side flow rate regulation valve for controlling the flow rate of the verification gas to make a verification gas flow rate measured value measured by the verification-side mass flow controller agree with a set flow rate are connected in series to each other, and the verification gas input valve, the verification-side mass flow controller, and the verification-side flow rate regulation valve are arranged in parallel to the shutoff valve.

The above configured flow rate verification unit is connected to the integrated gas unit via the connection part in a detachable manner. In this configuration, the volume between the flow rate regulation valve of the integrated gas unit and the shutoff valve could vary depending on a connected state of the integrated gas unit to the connection part. The above configured flow rate verification unit is however configured such that the verification gas input valve, the verification-side mass flow controller, and the verification-side flow rate regulation valve are connected in series to each other and arranged in parallel to the shutoff valve. Accordingly, the flow rate verification unit does not need to use the mass flow controller of the integrated gas unit but only has to bring the shutoff valve into the valve-closed state and bring the verification gas input valve into the valve-open state to regulate the verification gas at the set flow rate and fill an upstream side of the shutoff valve with the gas through the verification-side mass flow controller and the verification-side flow rate regulation valve. The flow rate verification unit uses the pressure variation value per unit time of the pressure measured value measured by the pressure gauge and the temperature measured value measured by the thermometer in this configuration, thus calculating the volume between the flow rate regulation valve and the shutoff valve for performing the flow rate verification. Therefore, the above configured flow rate verification unit can be replaced among a plurality of the integrated gas units to perform the flow rate verification for each integrated gas unit.

(2) In the above configuration (1), preferably, the flow rate verification unit includes a calibration device configured to calibrate the verification-side mass flow controller by flowing the verification gas into the verification-side mass flow controller.

According to the above configured flow rate verification unit, the volume between the flow rate regulation valve and the shutoff valve can be accurately calculated, and thus the accuracy of the flow rate verification becomes stable.

(3) In the above configuration (1) or (2), preferably, the pressure gauge includes a first pressure gauge and a second pressure gauge which are different in measurement ranges.

In the above configured flow rate verification unit, any one of the first and second pressure gauges can be selected according to the control flow rate of the mass flow controller to be verified, and thus the verification time can be shortened without lowering the verification accuracy.

Effects of the Invention

The above configuration can provide a flow rate verification unit detachably attached to any one of a plurality of integrated gas units to perform flow rate verification for each of the plurality of integrated gas units.

MODE FOR CARRYING OUT THE INVENTION

Figure 1:
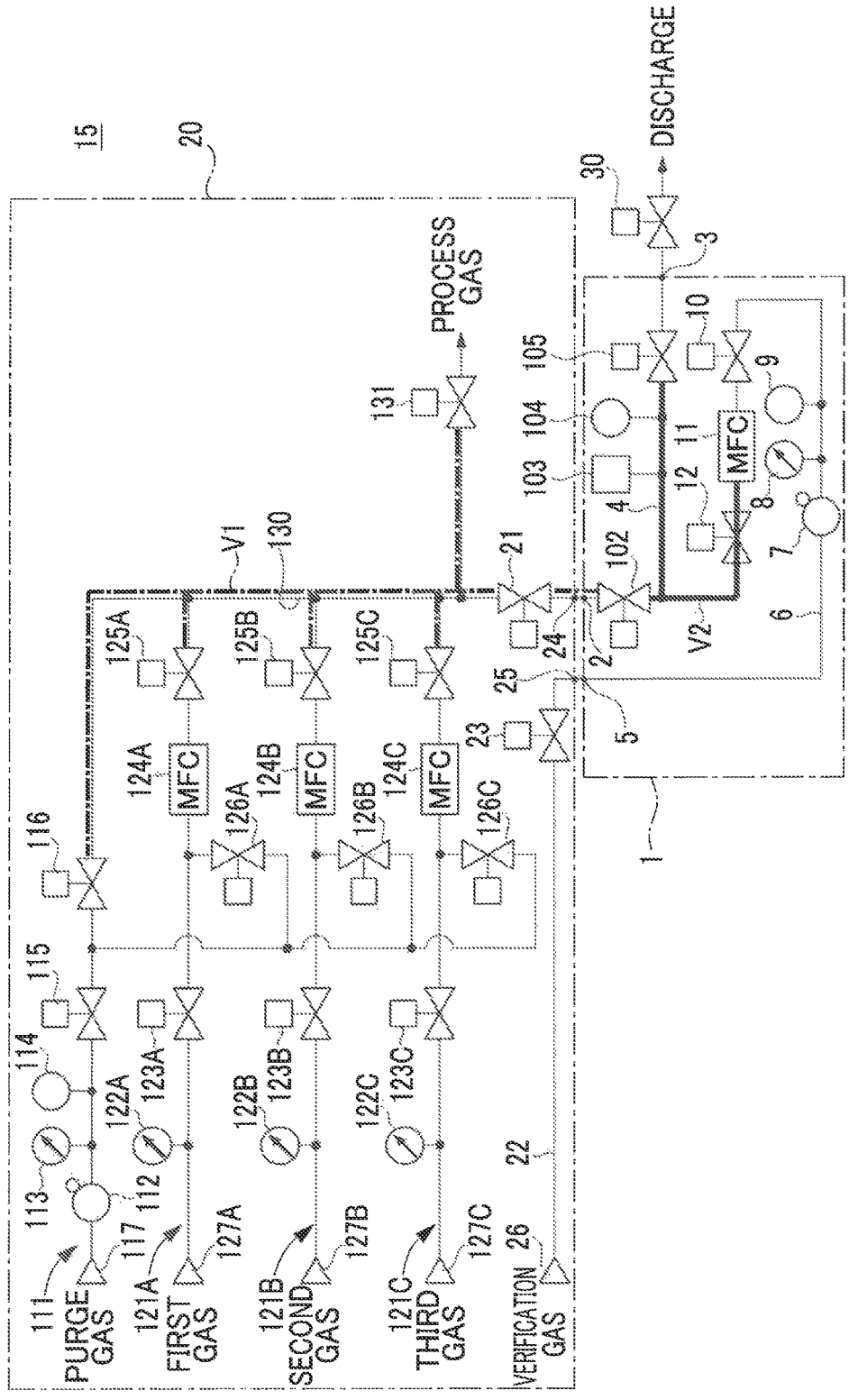
FIG. 1 is a circuit diagram of a flow rate verification system in which a flow rate verification unit according to a first embodiment of the present invention is connected to an integrated gas unit.
Figure 8:
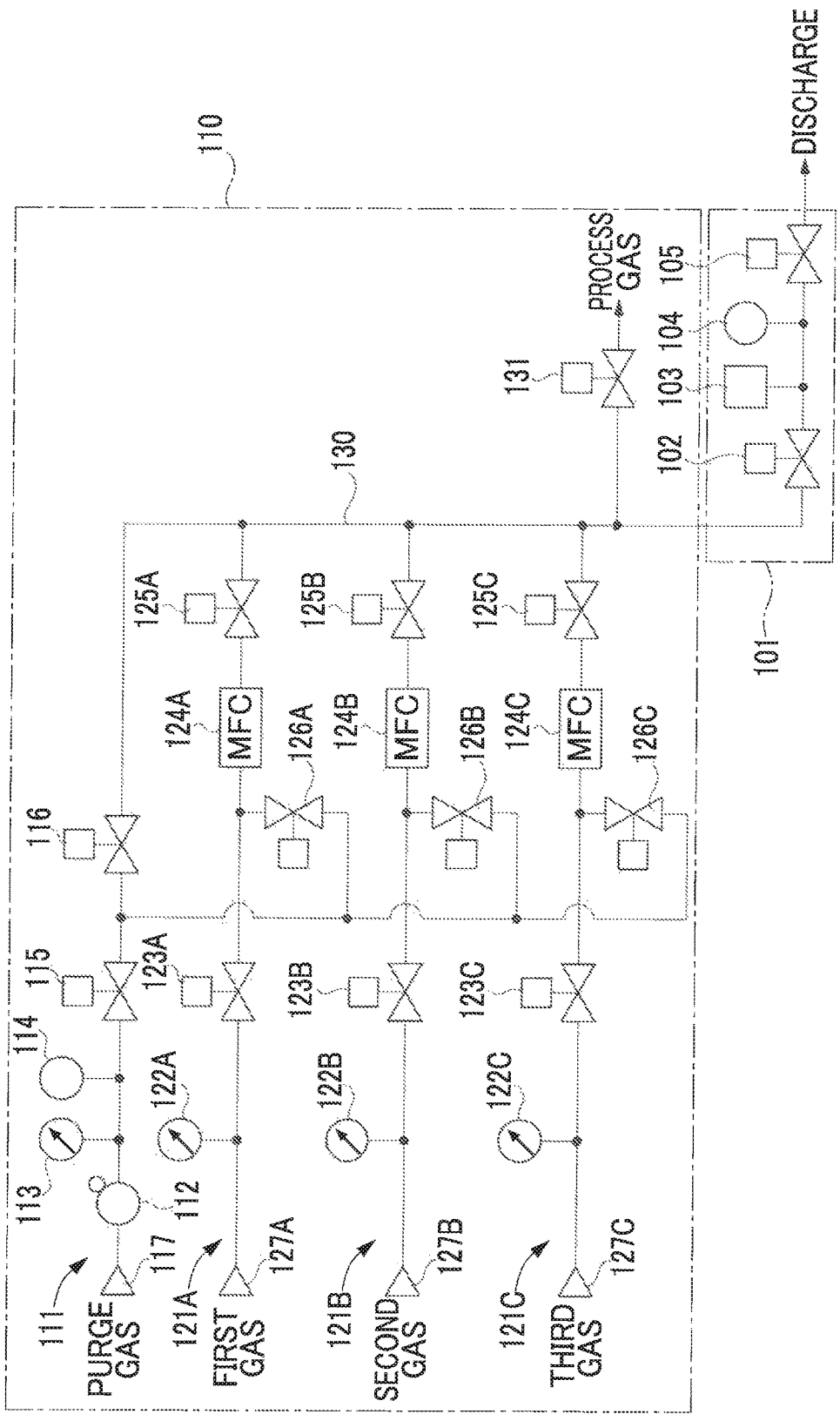
FIG. 8 is a circuit diagram of a conventional flow rate verification unit and an integrated gas unit.

A first embodiment embodying a flow rate verification unit of the present invention is now explained below with reference to the accompanying drawings. FIG. 1 is a circuit diagram of a flow rate verification system 15 in which a flow rate verification unit 1 according to the first embodiment of the present invention is connected to an integrated gas unit 20. In FIG. 1 and the following explanation, similar or identical parts or components to those of the conventional flow rate verification unit 101 and the conventional integrated gas unit 110 (see FIG. 8) are assigned the same reference signs as the reference signs in the conventional flow rate verification unit 101 and the conventional integrated gas unit 110, and those explanations are omitted as appropriate. The flow rate verification system 15 is configured such that the flow rate verification unit 1 is connected to the integrated gas unit 20 in a detachable manner so that a single flow rate verification unit 1 is detachably attached to any one of a plurality of integrated gas units 20 to perform the flow rate verification.

The flow rate verification unit 1 is provided with a verification passage 4 connecting a first verification-side connection part 2 and a second verification-side connection part 3, and a first shutoff valve 102, a pressure gauge 103, a thermometer 104, and a second shutoff valve 105 are arranged in series on the passage 4 in this order from a side of the first verification-side connection part 2. The flow rate verification unit 1 is provided with a merging passage 6 connecting the third verification-side connection part 5 to between the first shutoff valve 102 and the pressure gauge 103 on the verification passage 4. In the merging passage 6, a regulator 7, a Bourdon pressure gauge 8, a pressure gauge 9, a verification gas input valve 10, a verification-side mass flow controller 11, and a verification-side flow rate regulation valve 12 are arranged in series in this order from a side close to the third verification-side connection part 5. The regulator 7, the Bourdon pressure gauge 8, the pressure gauge 9, the verification gas input valve 10, the verification-side mass flow controller 11, and the verification-side flow rate regulation valve 12 are arranged in parallel to the pressure gauge 103, the thermometer 104, and the second shutoff valve 105 to enable filling of the verification gas into a pipe upstream of the second shutoff valve 105.

The integrated gas unit 20 includes a terminal end valve 21 placed in the common passage 130 to control open and close of a first integration-side connection part 24 which is provided at a terminal end portion of the common passage 130. The integrated gas unit 20 is provided with a verification gas line 22 connecting a verification gas input port 26 and a second integration-side connection part 25 and including a verification gas supply valve 23 which controls open and close of the second integration-side connection part 25. The remaining parts and components of the integrated gas unit 20 are similarly configured to those of the conventional integrated gas unit 110 (see FIG. 8). The verification gas input port 26 is connected to a verification gas supply source which supplies the verification gas (in the present embodiment, N2 gas). The verification gas supply source may be a purge gas supply source which is connected with the purge gas input port 117.

Figure 2:
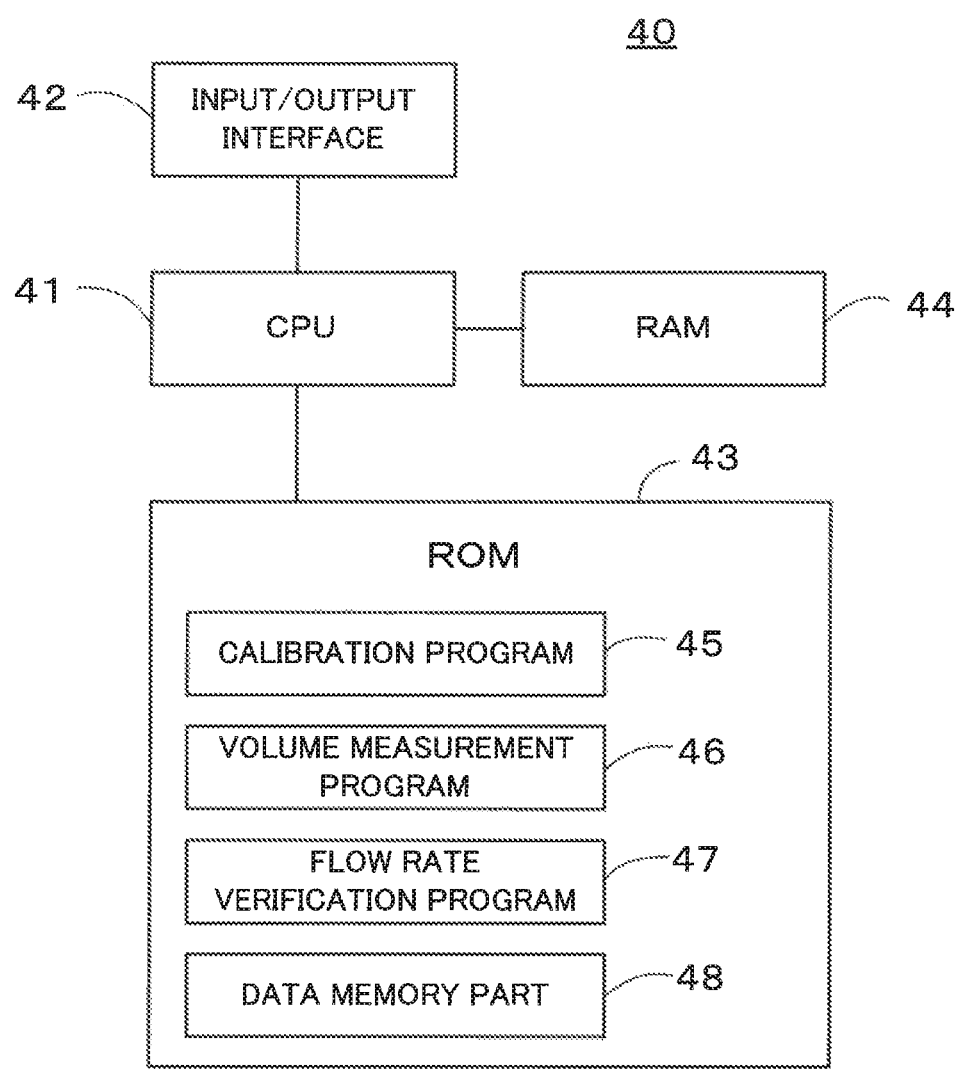
FIG. 2 is a schematic configurational view of a control device to control the flow rate verification unit shown in FIG. 1.

FIG. 2 is a schematic block diagram of a control device 40 to control the flow rate verification unit 1 shown in FIG. 1. The control device 40 is a well-known microcomputer and includes a central processing unit (CPU) 41, an input/output interface 42, an ROM 43, and an RAM 44. The ROM 43 is stored with various programs and data. The ROM 43 is stored with, for example, a calibration program 45, a volume measurement program 46, and a flow rate verification program 47. The ROM 43 is further provided with a data memory part 48 to store, for example, a set flow rate of each of the verification-side mass flow controller 11 and the mass flow controllers 124A to 124C, a measurement start pressure $P_0$ at the time of volume measurement and flow rate verification, a measurement time t for measuring the pressure, a volume (known volume) V2 among the first shutoff valve 102, the second shutoff valve 105, and the verification-side mass flow controller 11, and others, the volume V2 having been measured in advance.

The input/output interface 42 is connected to each of the first shutoff valve 102, the pressure gauge 103, the thermometer 104, the second shutoff valve 105, the Bourdon pressure gauge 8, the pressure gauge 9, the verification gas input valve 10, the verification-side mass flow controller 11, and the verification-side flow rate regulation valve 12 which are shown in FIG. 1. The input/output interface 42 is further connected with a controller (not shown) of the integrated gas unit 20. The control device 40 is configured to control open and close of the first and second purge valves 115 and 116, the gas input valves 123A to 123C, the flow rate regulation valves 125A to 125C, and the purge gas input valves 126A to 126C via the controller (not shown) of the integrated gas unit 20. The input/output interface 42 is further connected to a discharge valve 30 to allow the control device 40 to control open and close of the discharge valve 30.

Operation of the above-described flow rate verification unit 1 is now explained. The flow rate verification unit 1 is attached to the integrated gas unit 20 by connection of the first verification-side connection part 2 to the first integration-side connection part 24 and also by connection of the third verification-side connection part 5 to the second integration-side connection part 25 of the integrated gas unit 20. The second verification-side connection part 3 of the flow rate verification unit 1 is connected to the discharge valve 30. The flow rate verification unit 1 starts the flow rate verification by, for example, an operator's pushing of an instruction button to start flow rate verification.

Figure 3:
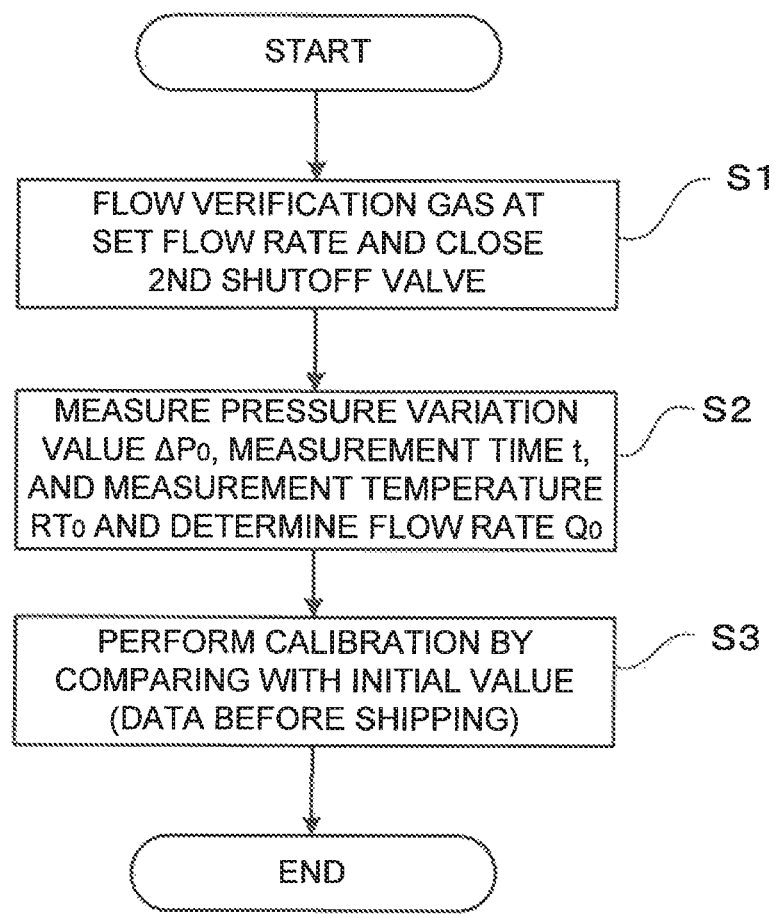
FIG. 3 is a flow chart of a calibration program for a verification-side mass flow controller shown in FIG. 2.

The control device 40 of the flow rate verification unit 1 firstly reads out the calibration program 45 from the ROM 43 and carries out the program. The verification gas is let flow through the verification-side mass flow controller 11 to calibrate the verification-side mass flow controller 11. This calibration of the verification-side mass flow controller 11 is performed to improve accuracy of measuring the volume V in a passage defined among the second purge valve 116, the flow rate regulation valves 125A to 125C, the common output valve 131, and the second shutoff valve 105. FIG. 3 is a flow chart showing the verification-side mass flow controller calibration program 45 shown in FIG. 2.

The control device 40 firstly executes the control to flow the verification gas in a state for a set flow rate and then close the second shutoff valve 105 in Step 1 (hereinafter, abbreviated as "S1"). Specifically, the control device 40 brings the verification gas supply valve 23, the verification gas input valve 10, the verification-side flow rate regulation valve 12, the second shutoff valve 105, and the discharge valve 30 into a valve-open state and brings the first shutoff valve 102 to a valve-closed state. Thus, the verification gas is allowed to flow into the discharge valve 30 via the regulator 7, the Bourdon pressure gauge 8, the pressure gauge 9, the verification gas input valve 10, the verification-side mass flow controller 11, the verification-side flow rate regulation valve 12, the pressure gauge 103, the thermometer 104, and the second shutoff valve 105. The control device 40 reads out the set flow rate from the data memory part 48 and operates the verification-side flow rate regulation valve 12 to make the flow rate measured value of the verification-side mass flow controller 11 agree with the set flow rate. When the flow rate measured value of the verification-side mass flow controller 11 stabilizes, the second shutoff valve 105 is brought into the valve-closed state.

In S2, subsequently, the control device 40 measures a pressure variation value $\Delta P_0$, a measurement time t, and a measurement temperature $RT_0$ and determines the flow rate using a gas state equation expressed by the following formula 1.

$$\text{Flow Rate} = \frac{\text{Pressure Variation Value} \times \text{Volume}}{\text{Measurement Time} \times \text{Temperature}} \quad [\text{Formula 1}]$$

Specifically, when the second shutoff valve 105 is closed, inner pressure in the verification passage 4 increases. Therefore, the control device 40 reads out the measurement start pressure $P_0$ and the measurement time t from the data memory part 48 and then measures the pressure $P_1$ after the measurement time t elapsed from the time when the pressure gauge 103 measured the measurement start pressure to calculate the pressure variation value $\Delta P_0$ ($\Delta P_0 = P_1 - P_0$). The control device 40 then receives the measured temperature $RT_0$ measured by the thermometer 104. The control device 40 further reads out the known volume V2 from the data memory part 48. The control device 40 substitutes the following values into the above formula 1, specifically, the pressure variation value $\Delta P_0$ for the "pressure variation value", the known volume V2 for the "volume", the measurement time t for the "measurement time", and the measured temperature $RT_0$ for the "temperature" to calculate the flow rate $Q_0$ of the verification-side mass flow controller 11.

Subsequently, in S3, the control device 40 carries out comparison with an initial value (data before shipping) and performs calibration. Specifically, the control device 40 compares the flow rate $Q_0$ calculated in S2 with the set flow rate. When a difference between the flow rate $Q_0$ and the set flow rate falls within an allowable range between the normal range and the abnormal range, the control device 40 corrects the set flow rate to eliminate the difference. When the difference between the flow rate $Q_0$ and the set flow rate is in the abnormal range, the control device 40 executes the control to make an indication to indicate that the verification-side mass flow controller 11 is abnormal. The calibration of the verification-side mass flow controller 11 is thus ended.

Figure 4:
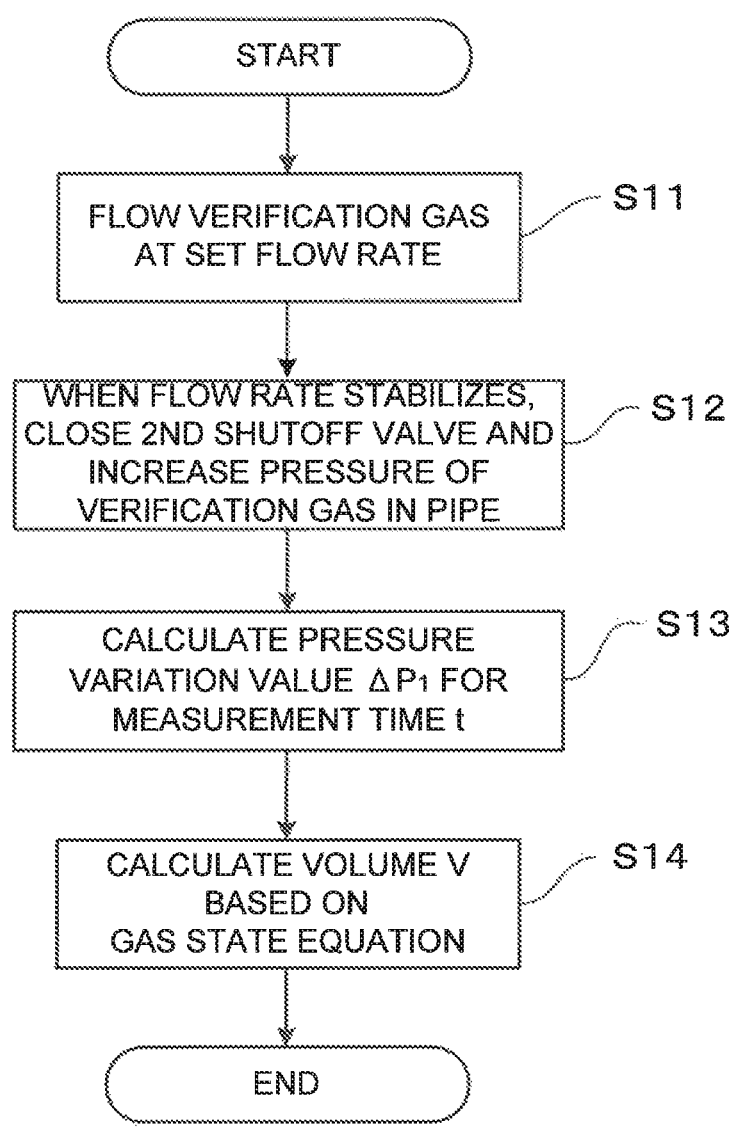
FIG. 4 is a flow chart of a volume measurement program shown in FIG. 2.

The control device 40 subsequently reads out the volume measurement program 46 from the ROM 43 and carries out the program to measure the volume V among the second purge valve 116, the flow rate regulation valves 125A to 125C, the common output valve 131, and the second shutoff valve 105 (the volume V is the sum of the known volume V2 and the tank volume V1 (see FIG. 1) among the second purge valve 116, the flow rate regulation valves 125A to 125C, the common output valve 131, and the first shutoff valve 102). The volume V varies among the integrated gas units 20 depending on the connected state of the first integration-side connection part 24 with each first verification-side connection part 2. Therefore, the volume V is measured as above to accurately obtain the volume V according to the relation with the connected integrated gas unit 20. FIG. 4 is a flow chart of the volume measurement program 46 in FIG. 2.

The control device 40 executes the control to flow the verification gas in a state for the set flow rate in S11. Specifically, the control device 40 brings the second purge valve 116, the flow rate regulation valves 125A to 125C, and the common output valve 131 into the valve-closed state and brings the verification gas supply valve 23, the gas input valve 10, the verification-side flow rate regulation valve 12, the first shutoff valve 102, the second shutoff valve 105, the discharge valve 30, and the terminal end valve 21 into the valve-open state, thereby allowing the verification gas to flow. At this time, the verification-side flow rate regulation valve 12 is operated to make the flow rate measured value of the verification-side mass flow controller 11 agree with the set flow rate stored in the data memory part 48.

When the flow rate stabilizes, the control device 40 closes the second shutoff valve 105 to increase the pressure of the verification gas inside a pipe in S12. To be specific, when the flow rate measured value of the verification-side mass flow controller 11 stabilizes, the control device 40 brings the second shutoff valve 105 into the valve-closed state to stop discharging the verification gas. Thus, the inner pressure in each of the common passage 130 and the verification passage 4 is increased.

In S13, the control device 40 measures the pressure variation value $\Delta P_1$ for the measurement time t. Specifically, the control device 40 measures the measurement start pressure $P_0$ by the pressure gauge 103 after closing the second shutoff valve 105, and subsequently measures the pressure $P_2$ by the pressure gauge 103 at the time of lapse of the measurement time t from the time of measuring the pressure $P_0$. The pressure variation value $\Delta P_1$ is calculated by subtracting the measurement start pressure $P_0$ from the pressure $P_2$ measured at the time when the measurement time t has elapsed.

In S14, the control device 40 calculates the volume V based on the gas state equation described as above in the formula 1. Namely, the control device 40 substitutes the pressure variation value $\Delta P_1$ calculated in S13 for the "pressure variation value", the set flow rate stored in the data memory part 48 for the "flow rate", the measurement time t stored in the data memory part 48 for the "measurement time", and a temperature measured value $RT_1$ measured by the thermometer 104 for the "temperature" in the above formula 1 to calculate the volume V. The verification-side mass flow controller 11 has been calibrated before measuring the volume, and hence the volume V can be accurately calculated. Thus, the control device 40 terminates the volume measurement processing.

Figure 5:
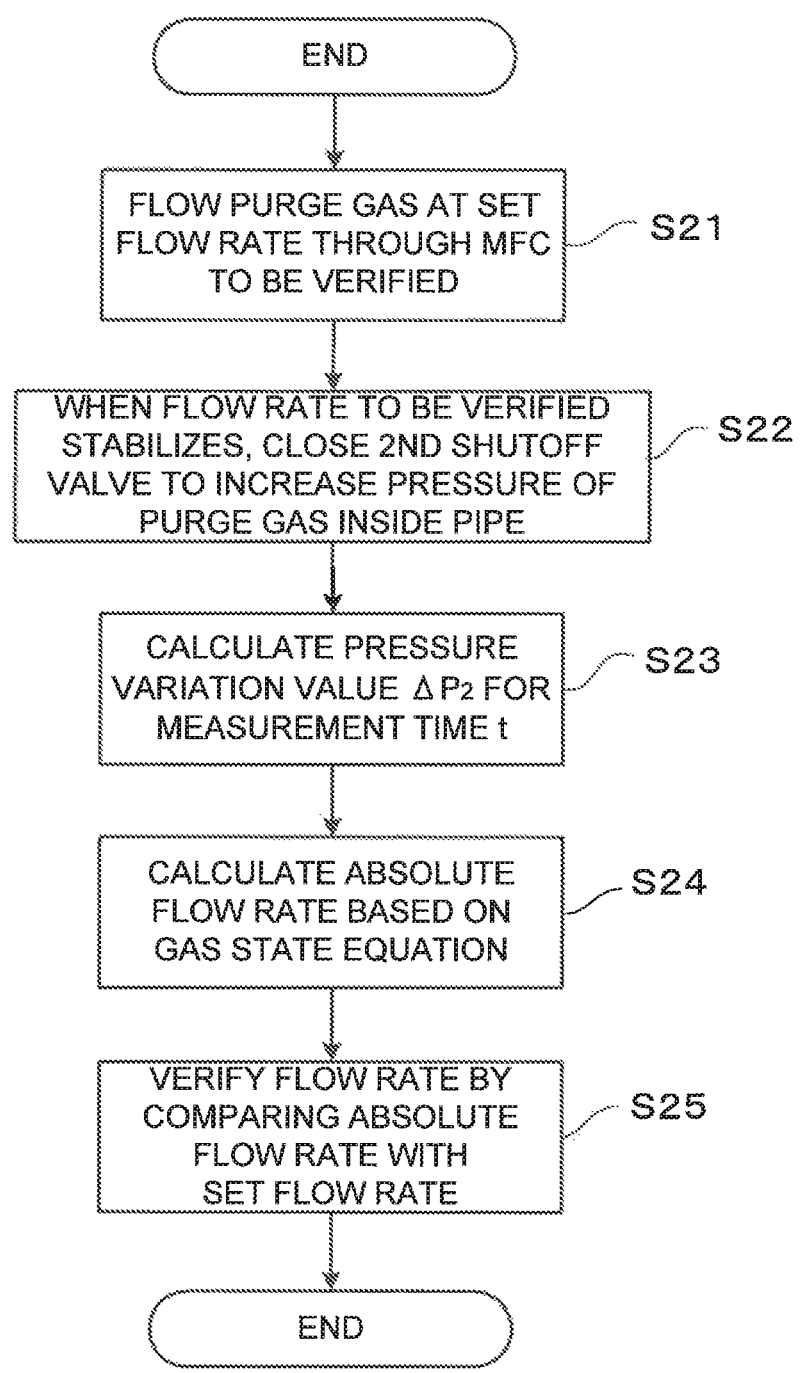
FIG. 5 is a flow chart of a flow rate verification program shown in FIG. 2.

The control device 40 subsequently reads out the flow rate verification program 47 from the ROM 43 and performs verification of the flow rate of each of the respective mass flow controllers 124A to 124C of the integrated gas unit 20. FIG. 5 is a flow chart of the flow rate verification program 47 in FIG. 2.

In S21, the control device 40 executes the control to flow the purge gas in a state for the set flow rate via the mass flow controller to be subjected to verification. Specifically, when the flow rate verification of the mass flow controller 124A is to be performed, for example, the control device 40 brings the first purge valve 115, the purge gas input valve 126A, the flow rate regulation valve 125A, the terminal end valve 21, the first shutoff valve 102, the second shutoff valve 105, and the discharge valve 30 into the valve-open state and brings the second purge valve 116, the gas input valves 123A to 123C, the flow rate regulation valves 125B and 125C, the purge gas input valves 126B and 126C, the verification gas supply valve 23, the verification gas input valve 10, the verification-side flow rate regulation valve 12, and the common output valve 131 into the valve-closed state, and allows the purge gas to flow in the mass flow controller 124A.

In S22, when the flow rate of the mass flow controller 124A stabilizes, the control device 40 closes the second shutoff valve 105 to increase the pressure of the purge gas inside the pipe. To be more specific, when the flow rate measured value of the mass flow controller 124A stabilizes, the control device 40 executes the control to close the second shutoff valve 105 to fill up the common passage 130 and the verification passage 4 with the purge gas to increase the pressure at the volume V.

In S23, the control device 40 calculates the pressure variation value $\Delta P_2$ for the measurement time t. Specifically, when the pressure measured value measured by the pressure gauge 103 reaches the measurement start pressure $P_0$ having been stored in the data memory part 48, the control device 40 measures a pressure $P_3$ at the time of lapse of the measurement time t by the pressure gauge 103. The pressure variation value $\Delta P_2$ is thus calculated by subtracting the measurement start pressure $P_0$ from the measured pressure $P_3$.

In S24, the control device 40 calculates the absolute flow rate $Q_2$ based on the gas state equation described as above in the formula 1. To be specific, the absolute flow rate $Q_2$ is calculated by the above formula 1 by substituting the volume V measured by the processing described in FIG. 4 for the "volume", the pressure variation value $\Delta P_2$ calculated in S23 for the "pressure variation value", the measurement time t stored in the data memory part 48 for the "measurement time", and a temperature measured value $RT_2$ measured by the thermometer for the "temperature".

In S25, the control device 40 carries out the flow rate verification by comparing the absolute flow rate $Q_2$ with the set flow rate. Specifically, the control device 40 obtains a difference between the current set flow rate and the absolute flow rate $Q_2$ calculated in S24. When this difference is within the normal range, the control device 40 makes an indication to indicate termination of the verification. When the difference between the current set flow rate and the absolute flow rate $Q_2$ is in an allowable range between the normal range and the abnormal range, the control device 40 corrects the set flow rate of the mass flow controller 124A and indicates termination of the verification. When the difference between the current set flow rate and the absolute flow rate $Q_2$ is in the abnormal range, the control device 40 indicates an instruction to replace the mass flow controller 124A. Thus, the control device 40 terminates the flow rate verification.

After the termination of the flow rate verification, all the valves in the integrated gas unit 20 and in the flow rate verification unit 1 are closed, and then the first and third verification-side connection parts 2 and 5 are respectively disconnected from the first and second integration-side connection parts 24 and 25 and in addition the second verification-side connection part 3 is disconnected from the discharge valve 30, and thus the flow rate verification unit 1 is detached from the integrated gas unit 20.

Subsequently, the flow rate verification unit 1 is attached to another one of the integrated gas units 20 in a similar manner to the above and then carries out calibration of the verification-side mass flow controller 11 and measurement of the volume V for performing the flow rate verification. At this time, depending on the connected state of the first verification-side connection part 2, the volume V of the integrated gas unit 20 subjected to be verified could be different from the volume V of the former verified integrated gas unit 20. However, the flow rate verification unit 1 calculates the volume V of the latter integrated gas unit 20 by use of the verification-side mass flow controller 11, and accordingly, the flow rate verification of the latter integrated gas unit 20 can also be performed accurately.

As explained above, the flow rate verification unit 1 of the present embodiment is configured to verify the flow rate of each of the mass flow controllers 124A to 124C one at a time, and the integrated gas unit 20 is configured such that the first to third gas supply lines 121A to 121C respectively are provided with the mass flow controllers 124A to 124C and the flow rate regulation valves 125A to 125C and are arranged in parallel. The flow rate verification unit 1 includes the pressure gauge 103, the thermometer 104, and the second shutoff valve 105 which are arranged in series and the flow rate verification unit 1 performs the flow rate verification by calculating the volume V in the passage defined among the flow rate regulation valves 125A to 125C and the second shutoff valve 105 from the pressure variation value per unit time of the pressure measured value measured by the pressure gauge 103 and the temperature measured value measured by the thermometer 104 in a state in which the second shutoff valve 105 is closed. The flow rate verification unit 1 is further provided with the first verification-side connection part 2 provided upstream of the pressure gauge 103 and connected to the integrated gas unit 20 in a detachable manner, the verification gas input valve 10 to control input of the verification gas, the verification-side mass flow controller 11 to measure the flow rate of the verification gas, and the verification-side flow rate regulation valve 12 operative to make the verification-side flow rate measured value measured by the verification-side mass flow controller 11 agree with the set flow rate, which are connected in series, and the unit 1 is configured such that the verification gas input valve 10, the verification-side mass flow controller 11, and the verification-side flow rate regulation valve 12 are arranged in parallel to the second shutoff valve 105.

The thus configured flow rate verification unit 1 is connected to the integrated gas unit 20 via the first verification-side connection part 2 in a detachable manner. Depending on the connected state of the first verification-side connection part 2 with the integrated gas unit 20, the volume V in a passage defined among the flow rate regulation valves 125A to 125C and the second shutoff valve 105 of the integrated gas unit 20 varies. However, the above-mentioned flow rate verification unit 1 is configured such that the verification-side gas input valve 10, the verification-side mass flow controller 11, and the verification-side flow rate regulation valve 12, which are connected in series, are arranged in parallel to the second shutoff valve 105. Accordingly, the flow rate verification unit 1 can regulate the verification gas at the set flow rate through the verification-side mass flow controller 11 and the verification-side flow rate regulation valve 12 and fill the passage upstream of the second shutoff valve 105 with the verification gas by closing the second shutoff valve 105 and opening the verification gas input valve 10 with no need of using the mass flow controllers 124A to 124C of the integrated gas unit 20. In the above control, the flow rate verification unit 1 utilizes the pressure variation value per unit time of the pressure measured value measured by the pressure gauge 103 and the temperature measured value measured by the thermometer 104 to calculate the volume V among the flow rate regulation valves 125A to 125C and the second shutoff valve 105 to perform the flow rate verification. Therefore, the above flow rate verification unit 1 can be detachably attached to a plurality of integrated gas units 20 to perform the flow rate verification.

The flow rate verification unit 1 of the present embodiment is further provided with the calibration program (on example of a calibration device) to calibrate the verification-side mass flow controller 11 by flowing the verification gas into the verification-side mass flow controller 11. Thus, the volume V can be accurately calculated, resulting in stability in accuracy of flow rate verification.

Figure 6:
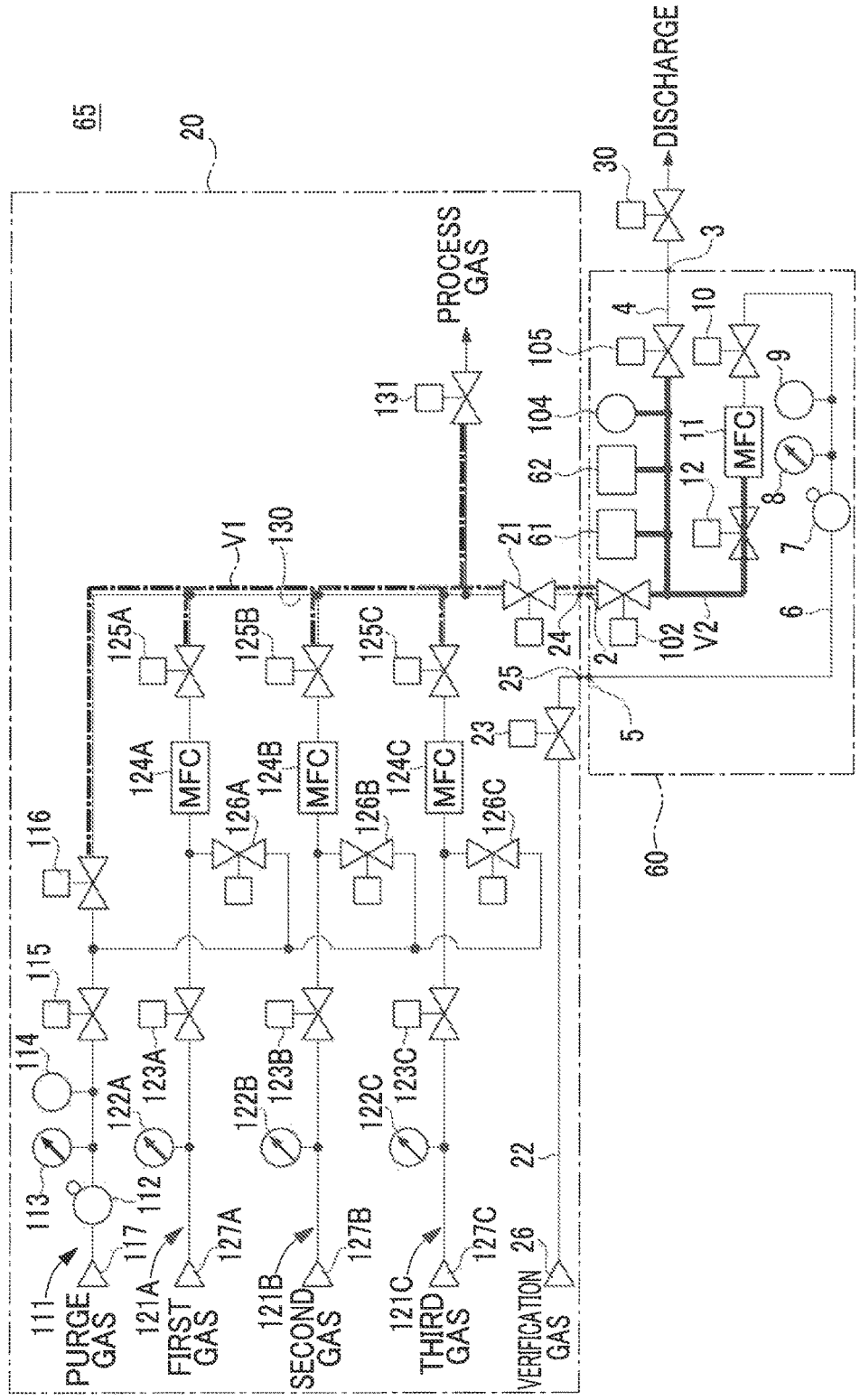
FIG. 6 is a circuit diagram of a flow rate verification system in which a flow rate verification unit according to a second embodiment of the present invention is connected to an integrated gas unit.

Next, a second embodiment of a flow rate verification unit of the present invention is explained. FIG. 6 is a circuit diagram of a flow rate verification system 65 in which a flow rate verification unit 60 according to the second embodiment of the present invention is connected to the integrated gas unit 20. The flow rate verification system 65 is configured similarly to the flow rate verification system 15 of the first embodiment except for that a first and second pressure gauges 61 and 62, which are different in their measurement ranges, are provided instead of the pressure gauge 103 of the first embodiment. In the following explanation, similar or identical parts or components to those of the first embodiment are assigned with the same reference signs as those in the first embodiment and their explanations are omitted as appropriate.

Figure 7:
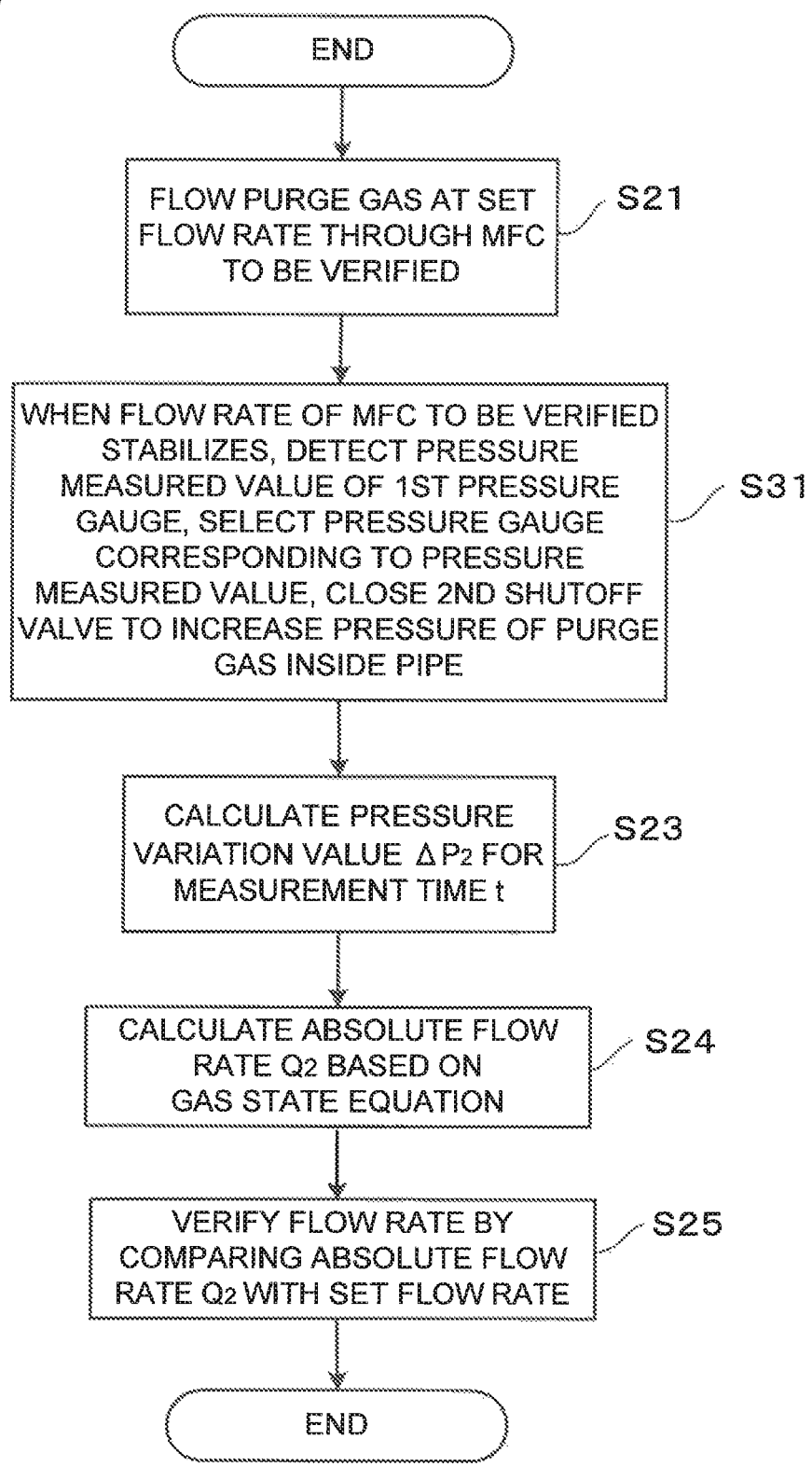
FIG. 7 is a flow chart of a flow rate verification program to be carried out by the control device to control the flow rate verification unit shown in FIG. 6.

FIG. 7 is a flow chart of a flow rate verification program carried out by the control device 40 to control the flow rate verification unit 60 in FIG. 6. The processing of the flow rate verification program shown in FIG. 7 is different from the processing of the flow rate verification program 47 of the first embodiment (see FIG. 5) only in the processing of S31. In S31, when the flow rate of a mass flow controller to be verified stabilizes, the control device 40 executes the control to detect a pressure measured value of the first pressure gauge 61 and selects one of the pressure gauges 61 and 62 based on the pressure measured value. Subsequently, the second shutoff valve 105 is closed to increase the pressure of the purge gas inside the pipe.

To be specific, when the flow rate verification of the mass flow controller 124A is to be performed, for example, in S31, the first purge valve 115, the purge gas input valve 126A, the flow rate regulation valve 125A, the terminal end valve 21, the first shutoff valve 102, the second shutoff valve 105, and the discharge valve 30 are brought into the valve-open state, and the second purge valve 116, the gas input valves 123A to 123C, the flow rate regulation valves 125B and 125C, the purge gas input valves 126B and 126C, the verification gas supply valve 23, the verification gas input valve 10, the verification-side flow rate regulation valve 12, and the common output valve 131 are brought into the valve-closed state. Thus, the purge gas is let flow to the mass flow controller 124A. When the flow rate of the mass flow controller 124A stabilizes, the pressure measured value is input from the first pressure gauge 61. When the pressure measured value of the first pressure gauge 61 is within the measurement range of the first pressure gauge 61, the first pressure gauge 61 is selected. When the pressure measured value of the first pressure gauge 61 is out of the measurement range of the first pressure gauge 61, on the other hand, the second pressure gauge 62 is selected. The following processing after selection of the pressure gauge is similar to the flow rate verification of the first embodiment, and hence the explanation is omitted.

Even if the volume V is same, each integrated gas unit 20 is different in its time for supplying the purge gas to fill the volume V depending on the control flow rate of the mass flow controllers 124A to 124C. For example, an integrated gas unit 20, in which the control flow rate of the mass flow controllers 124A to 124C is 1 sccm or more and less than 10 sccm, takes more time to supply the purge gas to fill the volume V than another integrated gas unit 20 in which the control flow rate is 10 sccm or more and less than 1000 sccm.

To address the above, the present embodiment is configured such that, when the control flow rate of the mass flow controller 124A is 1 sccm or more and less than 10 sccm for example and the first pressure gauge 61 is not able to measure the pressure, the flow rate verification unit 60 selects the second pressure gauge 62 having the measurement range lower than the first pressure gauge 61 and performs the flow rate verification using the pressure measured value measured by the second pressure gauge 62. When the control flow rate of the mass flow controller 124A is 10 sccm or more and less than 1000 sccm and the first pressure gauge 61 is able to measure the pressure, the first pressure gauge 61 is selected and the flow rate verification is performed with the pressure measured value measured by the first pressure gauge 61. Therefore, according to the flow rate verification unit 60 of the present embodiment, either one of the first pressure gauge 61 and the second pressure gauge 62 can be selected depending on the control flow rate of the mass flow controller 124A to be verified, and thus the verification time can be shortened without lowering the verification accuracy.

The present invention may be modified in various ways without being limited to the above embodiments. For example, in the above embodiment, the verification gas line 22 is provided in the integrated gas unit 20 to supply the verification gas to the flow rate verification unit 1. As one alternative to this, the flow rate verification unit 1 may be configured to dispense with the regulator 7, the Bourdon pressure gauge 8, and the pressure gauge 9 while the integrated gas unit 20 is provided with a pipe connecting the pressure gauge 114 of the purge gas line 111 with the first purge valve 115 and a supply valve placed on the pipe so that the third verification-side connection part 5 of the flow rate verification unit 1 is connected to a part of the pipe downstream of the supply valve. In this example, the calibration and the volume measurement of the verification-side mass flow controller 11 is performed by inputting the purge gas from the purge gas line 111. This configuration achieves reduction in components mounted in the flow rate verification unit 1 and further achieves reduction in cost.

For example, in the above embodiments, the control flow rate of the mass flow controllers 124A to 124C is stored in the data memory part 48. As one alternative to this, the control device 40 may input the flow rate value to a controller (not shown) of the integrated gas unit.

For example, in the above second embodiment, the first and second pressure gauges 61 and 62 which are different in the measurement range are used. As one alternative to this, two pieces of pressure gauges having the same measurement range may be arranged between the first and second shutoff valves 102 and 105 to compare the pressure measured values.

For example, the terminal end valve 21, the verification gas supply valve 23, and the discharge valve 30 may be omitted, and each terminal end of the common passage 130, the verification gas line 22, and the verification passage 4 may be sealed with a sealing plug and others.

REFERENCE SIGNS LIST

1, 60 Flow rate verification unit
2 First verification-side connection part (one example of Connection part)
10 Verification gas input valve
11 Verification-side mass flow controller
12 Verification-side flow rate regulation valve
20 Integrated gas unit
45 Calibration program (one example of Calibration member)
61, 62 First and second pressure gauges
103 Pressure gauge
104 Thermometer
105 Second shutoff valve (one example of Shutoff valve)
121A to 121C First to third gas supply line
124A to 124C Mass flow controller
125A to 125C Flow rate regulation valve The invention claimed:

1. A flow rate verification unit to perform flow rate verification for an integrated gas unit provided with a plurality of gas supply lines arranged in parallel, each of the gas supply lines including a mass flow controller and a flow rate regulation valve, the flow rate verification unit comprising a pressure gauge, a thermometer, and a shutoff valve which are arranged in series, and the flow rate verification unit being configured to verify a flow rate of each mass flow controller one at a time by calculating a volume between the flow rate regulation valve and the shutoff valve by use of a pressure variation value of a pressure measured value per unit time measured by the pressure gauge and a temperature measured value measured by the thermometer in a state in which the shutoff valve is closed, wherein the flow rate verification unit further includes a first connection part provided on an upstream side of the pressure gauge, the first connection part being configured to be detachably connected to a common passage that is provided in the integrated gas unit and connected with the plurality of the gas supply lines, and a second connection part connected to a verification gas line provided in the integrated gas unit in a detachable manner, a verification gas input valve for controlling verification gas that is input from the verification gas line through the second connection part, a verification-side mass flow controller for measuring a flow rate of the verification gas, and a verification-side flow rate regulation valve for controlling the flow rate of the verification gas to make a verification gas flow rate measured value measured by the verification-side mass flow controller agree with a set flow rate are connected in series to each other, and the verification gas input valve, the verification-side mass flow controller, and the verification-side flow rate regulation valve are arranged in parallel to the shutoff valve.

2. The flow rate verification unit according to claim 1 including a processor programmed to calibrate the verification-side mass flow controller by flowing the verification gas into the verification-side mass flow controller.

3. The flow rate verification unit according to claim 2, wherein the pressure gauge includes a first pressure gauge and a second pressure gauge which are different in measurement ranges.

4. The flow rate verification unit according to claim 1, wherein the pressure gauge includes a first pressure gauge and a second pressure gauge which are different in measurement ranges.

* * * * *